(12) United States Patent
Katagiri et al.

(10) Patent No.: US 11,169,162 B2
(45) Date of Patent: Nov. 9, 2021

(54) KIT AND METHOD FOR MEASURING PROSTAGLANDIN E-MAJOR URINARY METABOLITE

(71) Applicant: FUJIREBIO INC., Tokyo (JP)

(72) Inventors: Noriko Katagiri, Tokyo (JP); Shintaro Yagi, Tokyo (JP)

(73) Assignee: FUJIREBIO INC., Tokyo (JP)

( * ) Notice: Subject to any disclaimer, the term of this patent is extended or adjusted under 35 U.S.C. 154(b) by 84 days.

(21) Appl. No.: 16/084,634

(22) PCT Filed: Mar. 13, 2017

(86) PCT No.: PCT/JP2017/009963
§ 371 (c)(1),
(2) Date: Sep. 13, 2018

(87) PCT Pub. No.: WO2017/159612
PCT Pub. Date: Sep. 21, 2017

(65) Prior Publication Data
US 2019/0072571 A1    Mar. 7, 2019

(30) Foreign Application Priority Data

Mar. 14, 2016   (JP) .............................. JP2016-049961

(51) Int. Cl.
*G01N 33/88*   (2006.01)
*G01N 33/543*  (2006.01)

(52) U.S. Cl.
CPC ....... *G01N 33/88* (2013.01); *G01N 33/54393* (2013.01)

(58) Field of Classification Search
CPC .............. G01N 33/88; G01N 35/0098; G01N 33/54326; G01N 33/54333; G01N 33/5434; G01N 27/745
See application file for complete search history.

(56) References Cited

U.S. PATENT DOCUMENTS

| | | | | |
|---|---|---|---|---|
| 4,208,479 A * | 6/1980 | Zuk | ...................... | C07J 41/0016 435/7.9 |
| 5,925,573 A * | 7/1999 | Colin | ............... | G01N 33/54333 209/213 |
| 5,958,339 A * | 9/1999 | Belly | ............... | G01N 33/54386 422/422 |
| 6,723,510 B2 * | 4/2004 | Lubenow | ................. | C07K 1/22 382/129 |
| 2005/0019755 A1 * | 1/2005 | Marchessault | ......... | B82Y 25/00 435/5 |
| 2009/0130775 A1 * | 5/2009 | Fujiwara | ................ | G01N 33/88 436/501 |
| 2018/0136241 A1 * | 5/2018 | Murata | .............. | G01N 33/6893 |

FOREIGN PATENT DOCUMENTS

EP         0166583 B1 *  9/1991    ............. G01N 33/88

OTHER PUBLICATIONS

Definition of the term "solution" (2014). In M. Clugston, The Penguin dictionary of science (4th ed.). Penguin. Credo Reference: https://search.credoreference.com/content/entry/penguinscience/solution/0, retrieved on Jun. 8, 2020 (2 pages) (Year: 2014).*
Mohan, Chandra. "Calbiochem: Buffers" (2003), retrieved from http://wolfson.huji.ac.il/purification/PDF/Buffers/Calbiochem_Buffers_Booklet.pdf on Jun. 8, 2020, 37 pages (Year: 2003).*
Demers et al. "Development and validation of a radioimmunoassay for prostaglandin E2 metabolite levels in plasma" J Clin Endocrinol Metab. Jul. 1983;57(1):101-6. doi: 10.1210/jcem-57-1-101 (Year: 1983).*
Arai et al. "Prostaglandin E-Major Urinary Metabolite as a Reliable Surrogate Marker for Mucosal Inflammation in Ulcerative Colitis" Inflamm Bowel Dis. Jul. 2014;20(7):1208-16. DOI 10.1097/MIB.0000000000000062 (Year: 2014).*
Okayasu et al. "Significant Increase of Prostaglandin E-Major Urinary Metabolite in Male Smokers: A Screening Study of Age and Gender Differences Using a Simple Radioimmunoassay" Journal of Clinical Laboratory Analysis 28: 32-41 (2014) (Year: 2014).*

* cited by examiner

*Primary Examiner* — Christine Foster
(74) *Attorney, Agent, or Firm* — Birch, Stewart, Kolasch & Birch, LLP

(57) ABSTRACT

Disclosed is a method of measuring the prostaglandin E main urinary metabolite (PGE-MUM), in which a mixture solution of a urine sample treated with alkali can directly be subjected to an antigen-antibody reaction system in an immunoassay of PGE-MUM, without neutralization and dilution followed by dispensation. The method of measuring PGE-MUM includes the steps of: a) mixing a urine sample with an alkaline aqueous solution, and b) subjecting the mixture solution resulting from a) to an immunoassay using a bicyclo PGE-MUM-immobilized or anti-bicyclo PGE-MUM antibody-immobilized solid phase to measure PGE-MUM in the urine sample, wherein the immunoassay is performed in a weakly-acidic basal buffer solution in the presence of a second pH buffering agent which exerts a buffering effect in the basic range and is different from the pH buffering agent contained in the basal buffer solution, and in the presence of a cationic surfactant.

15 Claims, 4 Drawing Sheets

KIT AND METHOD FOR MEASURING PROSTAGLANDIN E-MAJOR URINARY METABOLITE

TECHNICAL FIELD

The present invention relates to a method of measuring the prostaglandin E main urinary metabolite and a kit for the measurement of the prostaglandin E main urinary metabolite.

BACKGROUND ART

Ulcerative colitis is known as a refractory inflammatory disease and the number of patients with this condition is sharply increasing in recent years and was 166,060 (the sum of the numbers of issued medical treatment beneficiary certificates and issued registrant's certificates of registration for ulcerative colitis patients) at the end of the fiscal year 2013. Ulcerative colitis is an inflammatory disease of the large intestine, which causes inflammation and ulceration of the colorectal mucosa and whose characteristic symptoms are diarrhea, with or without bleeding, and frequent abdominal cramping. The lesion of ulcerative colitis has a tendency to extend upward and continuously from the rectum and extends from the rectum to the whole colon at most. Involvement of enteric bacteria, abnormal autoimmune reaction resulting from immune dysfunction, or involvement of change in dietary habits is suspected to be a cause of this disease, but it still remains unclear. Ulcerative colitis is diagnosed based on persistent or recurrent mucous and bloody stool episode as a clinical manifestation or on previous manifestation of the symptom. Furthermore, endoscopy of the colon or the sigmoid colon is additionally employed, and barium enema X-ray examination and full colonoscopy, both of which are state zwitterionic of the art and also highly costly, are carried out as necessary. First, the data obtained from the clinical manifestation is analyzed to select an optimal therapy, such as to determine the necessity of surgery, to select a therapeutic agent, and to determine whether the administration of the therapeutic agent is discontinued or not, and then endoscopy is further carried out to identify the disease state. However, endoscopy has been a procedure that also carries a risk of bleeding due to perforation or damage of the intestinal mucosa in the active stage of ulcerative colitis, and causes a huge economic burden on the health care system as well as physical and mental burdens on examined patients when the procedure is repeatedly applied.

Meanwhile, interstitial pneumonia is known as one of the refractory inflammatory diseases. The term "interstitial pneumonia" is a collective term for conditions which finally cause development of alveolar fibrosis in association with inflammation of the interstitial tissue, and conditions including, for example, idiopathic pulmonary fibrosis, nonspecific interstitial pneumonia, and cryptogenic organizing pneumonia are known. The mechanism to develop interstitial pneumonia remains to be fully elucidated, and a high level of experience is required to diagnose interstitial pneumonia, which brings about a difficulty that, for example, the condition of a patient and the results from analysis of various collected data should be comprehensively considered in the diagnosis of individual cases. To solve the above problem, the relationship between the measured amount of osteopontin in plasma and the symptoms of interstitial pneumonia has been studied (Patent Document 1). Additionally, for example, Surfactant Protein-D (SP-D), Surfactant Protein-A (SP-A), and sialylated carbohydrate antigen KL-6 are known as markers for diagnosing symptoms of interstitial pneumonia.

However, those markers are detected as a result of advanced symptoms of interstitial pneumonia and, therefore, a method depending on these markers is found to be not necessarily appropriate as a means of diagnosing the stage of interstitial pneumonia.

Prostaglandins (hereinafter referred to as PGs) and derivatives thereof are reported to have relations with various pathologies involving inflammation in living bodies, and methods to measure small quantities of PGs by simple operation are known. Examples of the quantification method include gas chromatography-mass spectrometry (GC/MS), buffer chromatography-mass spectrometry (LC/MS/MS), radioimmunoassay (RIA), enzyme immunoassay (EIA), and the like. Prostaglandin E2 (PGE) is known as a chemical mediator involved in inflammation in living bodies and a method of measuring its main metabolite in urine (PGE Main Urinary Metabolite, hereinafter referred to as "PGE-MUM") by a competitive enzyme immunoassay has been reported (Patent Document 2).

With regard to the above-mentioned PGE-MUM, there has been an attempt to correlate the measured values of PGE-MUM in urine samples obtained from ulcerative colitis patients with the total scores (modified Talstad scores) of numerically represented plural clinical manifestations (clinical disease activities) in the same patients (Non-Patent Document 1). It was found that measurement of PGE-MUM in urine from a patient with ulcerative colitis enabled to distinguish the patient's stage of ulcerative colitis in the pre-remission phase from that in the remission phase, which in turn enabled to more appropriately determine a time point at which medication for the disease is stopped (Patent Document 3). Moreover, it was found with regard to interstitial pneumonia that measurement of PGE-MUM in urine from a patient with interstitial pneumonia enabled to distinguish the patient's stage of interstitial pneumonia in the active phase from that in the non-active phase (Patent Document 3).

As described above, mass spectrometry and immunoassay are recited as exemplary PGE-MUM measurement methods, but immunoassay can be particularly more suitable in view of the simplicity of operation and the reproducibility. PGE-MUM is mainly composed of tetranor-PGE-M (Formula (I) below) and tetranor-PGA-M (Formula (II) below), either of which is unstable in water. As indicated in Patent Documents 1 and 3, when PGE-MUM is measured by an immunoassay, a urine sample is usually treated with alkali to convert PGE-MUM into a bicyclo derivative with a stable structure and then to perform the immunoassay. As indicated in the formula below, tetranor-PGE-M and tetranor-PGA-M can be converted into a bicyclo derivative with a stable structure (Formula (III) below) by alkaline treatment, which consequently enables to measure the concentration of PGE-MUM containing tetranor-PGE-M and tetranor-PGA-M together.

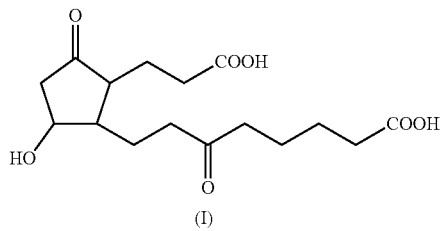

(I)

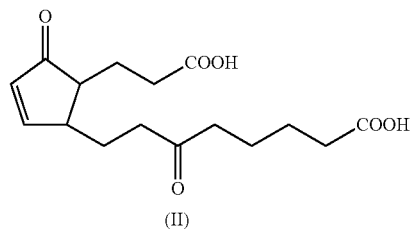

(II)

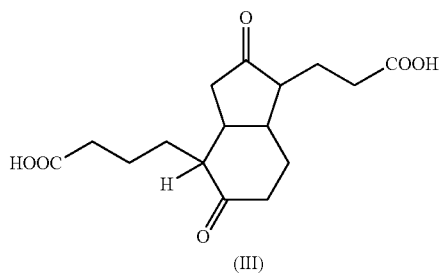

(III)

According to conventional methods as described in, for example, Patent Document 1, a urine sample is mixed and treated with a strong alkaline solution (for example, 1 N sodium hydroxide) and, therefore, the resulting mixture should be mixed with an acid (for example, 1 N hydrochloric acid) for neutralization to make the pH of the mixture suitable for a subsequent antigen-antibody reaction. Furthermore, an increased concentration of a salt (for example, sodium chloride) formed by the neutralization reaction may inhibit the subsequent antigen-antibody reaction and, therefore, the concentration of the salt should be diluted, for example, 10- to 20-fold with a buffer solution or the like. Problematically, those methods needed neutralization and dilution steps prior to sample measurement and thus were laborious, or those methods needed a dilution step and thus had a decreased sensitivity.

PRIOR ART DOCUMENTS

Patent Documents

Patent Document 1: JP 2005-030852 A
Patent Document 2: JP 61-11664 A
Patent Document 3: JP 4914347 B Non-Patent Document Non-Patent Document 1: Digestion (2000), 61: 201-206.

SUMMARY OF THE INVENTION

Problems to be Solved by the Invention

An object of the present invention is to provide a method of measuring the prostaglandin E main urinary metabolite (PGE-MUM), in which a mixture solution of a urine sample treated with alkali can directly be subjected to an antigen-antibody reaction system in an immunoassay of PGE-MUM, without neutralization and dilution followed by dispensation. Another object of the present invention is to provide a kit for the measurement of PGE-MUM, in which a mixture solution of a urine sample treated with alkali can directly be subjected to an antigen-antibody reaction system in the immunoassay of PGE-MUM, without neutralization and dilution followed by dispensation.

Means for Solving the Problems

The inventors intensively studied and consequently found that a mixture solution of a urine sample treated with alkali can be directly used in measurement, without neutralization and dilution steps, by performing an immunoassay in a weakly-acidic basal buffer solution in the presence of a second pH buffering agent which exerts a buffering effect in the basic range and is different from the pH buffering agent contained in the basal buffer solution. Moreover, the inventors found that by adding a cationic surfactant to the measurement system, PGE-MUM can be measured avoiding the influence of urinary contaminants produced by omitting the neutralization and dilution steps.

That is, the present invention provides a method of measuring the prostaglandin E main urinary metabolite (PGE-MUM), the method comprising the steps of:

a) mixing a urine sample with an alkaline aqueous solution, and b) subjecting the mixture solution resulting from a) to an immunoassay using a bicyclo PGE-MUM-immobilized or anti-bicyclo PGE-MUM antibody-immobilized solid phase to measure PGE-MUM in the urine sample, wherein the immunoassay is performed in a weakly-acidic basal buffer solution in the presence of a second pH buffering agent which exerts a buffering effect in the basic range and is different from the pH buffering agent contained in the basal buffer solution, and in the presence of a cationic surfactant.

The present invention also provides a kit for the measurement of urinary PGE-MUM comprising a solid phase on which bicyclo PGE-MUM or an anti-bicyclo PGE-MUM antibody is immobilized; a second pH buffering agent which exerts a buffering effect in the basic range in a weakly-acidic basal buffer solution which is different from the pH buffering agent contained in the basal buffer solution; and a cationic surfactant.

Effects of the Invention

According to the method and kit of the present invention, a mixture solution of a urine sample treated with alkali can directly be subjected to an antigen-antibody reaction system in an immunoassay of PGE-MUM, without neutralization and dilution steps followed by a dispensation step; steps of neutralizing and diluting an alkaline treated urinary mixture can be omitted and thus the sample processing process is simplified, which in turn enables the method and kit of the present invention to be applied, for example, to a multipurpose automated analyzer, moreover, the time required for the measurement may be shortened and the overall accuracy can be prevented from being reduced by frequent dispensation; and, furthermore, a dilution step is not included and, therefore, PGE-MUM can be examined with high sensitivity.

BRIEF DESCRIPTION OF THE DRAWINGS

FIG. 6A shows the correlation between the measured PGE-MUM values obtained by the conventional RIA (Reference Example 1) and those obtained by a CLEIA method with neutralization and dilution steps (Comparative Example 1). FIG. 6B shows the correlation between the measured PGE-MUM values obtained by the RIA and those obtained by a CLEIA method without neutralization and dilution steps (Comparative Example 2). FIG. 6C shows the correlation between the measured PGE-MUM values obtained by the RIA and those obtained in Example 1.

DETAILED DESCRIPTION OF THE INVENTION

Figure 1:
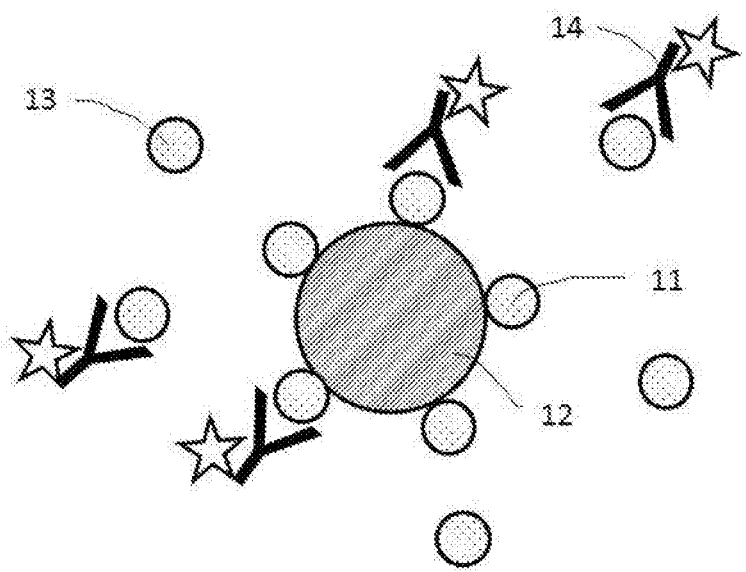
FIG. 1 shows a schematic diagram showing an antigen-antibody reaction system according to the first embodiment of the method according to the present invention.

As described above, the method of measuring PGE-MUM in urine according to the present invention comprises the steps of: a) mixing a urine sample with an alkaline aqueous solution, and b) subjecting the mixture solution resulting from a) to an immunoassay using a bicyclo PGE-MUM-immobilized or anti-bicyclo PGE-MUM antibody-immobilized solid phase to measure PGE-MUM in the urine sample.

The above-described alkaline treatment step a) per se is known, as described in Patent Document 1. The alkaline treatment is carried out by mixing a urine sample with an alkaline aqueous solution. A sodium hydroxide solution, a potassium hydroxide solution, calcium hydroxide, or barium hydroxide can be used as the alkaline solution used in this step, but the alkaline solution is not limited thereto as long as it is a strong alkaline aqueous solution. The normality of the alkaline aqueous solution can be 0.05 to 5 normal (N), preferably 0.1 to 4 N, and more preferably 0.2 to 2 N. The mixing ratio of a urine sample to a strong alkaline solution in the alkaline treatment can be 1:0.1 to 1:10, preferably 1:0.5 to 1:5, and more preferably 1:1 to 1:4.

The alkaline treatment can be performed by mixing a urine sample with a strong alkaline solution and leaving the resulting mixture to stand at 5 to 40° C., preferably 25 to 40° C., for 3 to 60 minutes, preferably 5 to 10 minutes.

In the subsequent step b), the mixture solution resulting from a) is subjected to an immunoassay using a bicyclo PGE-MUM-immobilized or anti-bicyclo PGE-MUM antibody-immobilized solid phase to measure PGE-MUM in the urine sample. The immunoassay using a bicyclo PGE-MUM-immobilized or anti-bicyclo PGE-MUM antibody-immobilized solid phase per se is known and will be described in the explanation of the various embodiments described below. Well known and usually used solid phases for immunoassays, such as particles (beads) and microplate wells, can be used as the solid phase. In cases where particles are used, magnetic particles (also referred to as magnetic beads) are preferable for easy recovery. Magnetic particles per se are well known in the field of immunoassay and are commercially available, so that commercial magnetic particles can preferably be used. For example, commercially available products such as commercial carboxylated magnetic particles and magnetic gelatin particles can preferably be used. The average diameter of magnetic particles is not particularly limited, but it is usually from about 1 μm to 10 μm.

An important feature of the method according to the present invention is to perform the immunoassay in a weakly-acidic basal buffer solution in the presence of a second pH buffering agent which exerts a buffering effect in the basic range and is different from the pH buffering agent contained in the basal buffer solution, and in the presence of a cationic surfactant.

The basal buffer solution is weakly acidic, and a buffer solution with a pH of 4.5 to 6.5 is preferably used, and a buffer solution with a pH of 5.0 to 6.0 is further preferably used. A buffer solution which has a buffer capacity at the pH range of about 4.0 to 7.5, such as a phosphate buffer, an acetate buffer, citric acid, maleic acid, malic acid and succinic acid, can preferably be used as the basal buffer solution. The use of an acidic buffer solution as the basal buffer solution enables to neutralize, at least partially, the strong alkaline treated sample obtained in the step a).

The above-described basal buffer solution to be used for performing the immunoassay comprises a second pH buffering agent which exerts a buffering effect in the basic range and is different from the pH buffering agent contained in the basal buffer solution. A buffering agent with a pKa (dissociation constant) of 6 to 10, preferably 6.5 to 9.5 and more preferably 8.0 to 9.0, can be used as the second pH buffering agent. Specific examples of the second pH buffering agent include Tricine, Bicine, Tris, imidazole, triethylamine, glycylglycine, and the like. The use of a buffering agent with a pKa within the above-described range enables to maintain the antigen-antibody reaction system at a pH within a range that does not inhibit the antigen-antibody reaction even if a urine sample mixed with a strong alkaline aqueous solution is directly added to the antigen-antibody reaction system. The concentration of the second buffering agent is not particularly limited, but it is appropriately selected depending on the type of the buffering agent, and the final concentration of the second buffering agent in a reaction buffer is usually from about 10 to 200 mM, particularly from 20 to 100 mM, in the immunoassay.

Examples of the cationic surfactant include alkyltrimethylammonium halides (alkyltrimethylammonium chlorides, alkyltrimethylammonium bromides), benzalkonium chloride, benzethonium chloride, alkylpyridinium chlorides, and the like, and alkyltrimethylammonium bromides or alkyltrimethylammonium chlorides, particularly alkyltrimethylammonium bromides, can preferably be used. The "alkyl" in an alkyltrimethylammonium halide is preferred to be a linear chain having 12 to 20 carbon atoms, particularly 14 to 18 carbon atoms.

When the concentration of a cationic surfactant is from 0.5 to 10 mM, particularly from 2 to 6 mM, the cationic surfactant is well dissolved in water and allows fully obtaining an effect to suppress an increase in background level due to urinary contaminants.

Particles can be used as the solid phase, as described above, and the particles can exist in the form of a particle buffer in which the particles are suspended in the basal buffer solution. In that case, the particle buffer comprises the cationic surfactant and the above-described second pH buffering agent, and the particle buffer is mixed with the mixture solution resulting from a). Magnetic particles are preferably used as the particles, as described above.

When a particle buffer containing the cationic surfactant is used, the particle buffer preferably further comprises a zwitterionic surfactant. Among cationic surfactants, especially those having a large number of carbon atoms are less soluble in water and tend to precipitate during a long-term storage and have a risk of adversely affecting the storage stability of the magnetic particle buffer. However, by adding a zwitterionic surfactant to the mixture, precipitation of the cationic surfactant can be suppressed. Examples of the zwitterionic surfactant include CHAPS, CHAPSO, N-alkyl sulfobetaine, alkylamino sulfobetaine, and the like. A zwitterionic surfactant contains an anionic group which may result in obtaining a falsely high value and, moreover, the effect of the cationic surfactant is abolished by adding an excess amount of a zwitterionic surfactant. Therefore, a zwitterionic surfactant is preferably added at a concentration less than an equal molar quantity of the cationic surfactant. The molar concentration of the zwitterionic surfactant is preferably 10 to 90, particularly preferably 20 to 80, and further preferably 25 to 50, taking the molar concentration of the cationic surfactant as 100.

In the method according to the present invention, additional steps of neutralizing and/or diluting the mixture solution resulting from a) (neutralization of the mixture solution resulting from a) with the basal buffer solution is not included in the "additional steps of neutralization and/or dilution") are not necessary and such steps are omitted, which is an advantage in view of work efficiency and work automation.

Various embodiments of the method according to the present invention will be described below with reference to the drawings.

First Embodiment

The first embodiment is a one-step competition assay in which a magnetic particle buffer containing bicyclo PGE-MUM antigen-immobilized magnetic particles is used with a labeled anti-bicyclo PGE-MUM antibody. FIG. 1 shows a schematic diagram of the antigen-antibody reaction system according to the first embodiment. Magnetic particles 12 as a solid phase linked to a bicyclo PGE-MUM antigen 11, a bicyclo PGE-MUM antigen 13 contained in a sample, and a labeled anti-bicyclo PGE-MUM antibody 14 are allowed to coexist and react together and then are washed to detect the antibody 14 bound to the magnetic particles 12 through the antigen 11. The higher the concentration of the antigen 13 in the sample, the smaller the amount of the labeled antibody 14 that has reacted with the antigen 11 immobilized on the magnetic particles 12 and thus the lower the obtained signal.

(1) Step a): Alkaline Treatment

The alkaline treatment is as described above.

(2) Step b): Mixing with a Magnetic Particle Buffer

The magnetic particle buffer comprises at least a second pH buffering agent, a bicyclo PGE-MUM antigen-immobilized magnetic particles, and a cationic surfactant. In the step b), the urinary mixture and the magnetic particle buffer are mixed together preferably at a ratio of 1:0.1 to 1:10, particularly preferably at 1:0.2 to 1:5 and further preferably at 1:0.5 to 1:2, in order to keep the pH of a reaction buffer within a proper range and to obtain sufficient measurement sensitivity. The mixed magnetic particle buffer may be left to stand at 5 to 40° C.

(2-1) Magnetic Particles

Magnetic particles on the surface of which bicyclo PGE-MUM has been immobilized are used. The antigen may be bound to the magnetic particles directly or through a binding protein such as KLG (mouse monoclonal IgG), serum albumin, or KLH. For example, carboxylated magnetic particles, magnetic gelatin particles and the like can be used as the magnetic particles.

(2-2) Particle Suspension, Second pH Buffering Agent, Cationic Surfactant, and Zwitterionic Surfactant The particle suspension, second pH buffering agent, cationic surfactant and zwitterionic surfactant are as described above.

(3) Step c): Reaction with Labeling Solution

The labeling solution comprises at least a labeled anti-bicyclo PGE-MUM antibody. The labeled antibody may be added immediately after the urinary mixture and the magnetic particle buffer are mixed, or after the urinary mixture mixed with the magnetic particle buffer is left to stand for a while. The ratio of the magnetic particle buffer (without the urinary mixture) to the labeling solution by volume is preferably 1:0.1 to 1:10, particularly preferably 1:0.2 to 1:5, and further preferably 1:0.5 to 1:2. The reaction among the sample, the magnetic particles and the labeled antibody is performed by leaving them to stand at 5 to 40° C., preferably 25 to 40° C., for 3 to 60 minutes, preferably 5 to 10 minutes.

(3-1) Dilution Buffer for Labeled Antibody

A labeled antibody dilution buffer constituting the labeling solution is preferably based on a buffer solution. The conditions of the labeled antibody dilution buffer, such as composition and pH, are not particularly limited as long as those conditions are suitable to stably preserve the labeled antibody, and any buffer solution commonly used in immunoassays can be used. The pH of the labeling solution is preferably from about 6 to 8 and particularly preferably from about 6.5 to 7.5, which is a condition close to that in living bodies.

(3-2) Labeled Antibody

The antibody which is used as a labeled antibody is not particularly limited as long as it can specifically bind to bicyclo PGE-MUM, and any of an antiserum, a polyclonal antibody and a monoclonal antibody can be used. However, a monoclonal antibody is more preferably used since monoclonal antibodies exhibiting the same performance can be stably produced.

The method for antibody labeling is not particularly limited as long as it is a labeling method available for an immunoassay, and any of known methods, such as enzymatic labeling (for example, horseradish peroxidase, and alkaline phosphatase), fluorescent labeling, and isotopic labeling, can be used. However, enzymatic labeling is preferably used since it does not need, for example, special equipment.

(4) Washing Step

Magnetic particles are collected and washed to remove components unbound to the particles. As the washing solution, a washing solution commonly used in an immunoassay, such as LUMIPULSE (registered trademark) (manufactured by Fujirebio Inc.), can be used.

(5) Detection Step

The labeled antibody bound to the magnetic particles is detected by an appropriate method according to the type of the used label; for example, when enzymatic labeling is used for antibody labeling, a substrate of the enzyme is added to detect the antibody. For example, in cases where an alkaline phosphatase (ALP) is used in the labeled antibody, a chemiluminescent enzyme immunoassay (CLEIA) system using 3-(2'-spiro-adamantane)-4-methoxy-4-(3'-phosphoryloxy) phenyl-1,2-dioxetane disodium salt (AMPPD) as a substrate of the enzyme can be used.

In the present embodiment, the antigen 13 may be a complex generated by a preceding reaction of bicyclo PGE-MUM with a molecule that specifically binds to the same (for example, anti-bicyclo PGE-MUM antibody). In this case, the labeled antibody 14 is preferably an antibody that specifically binds not to simple PGE-MUM but to the above complex.

Second Embodiment

Figure 2:
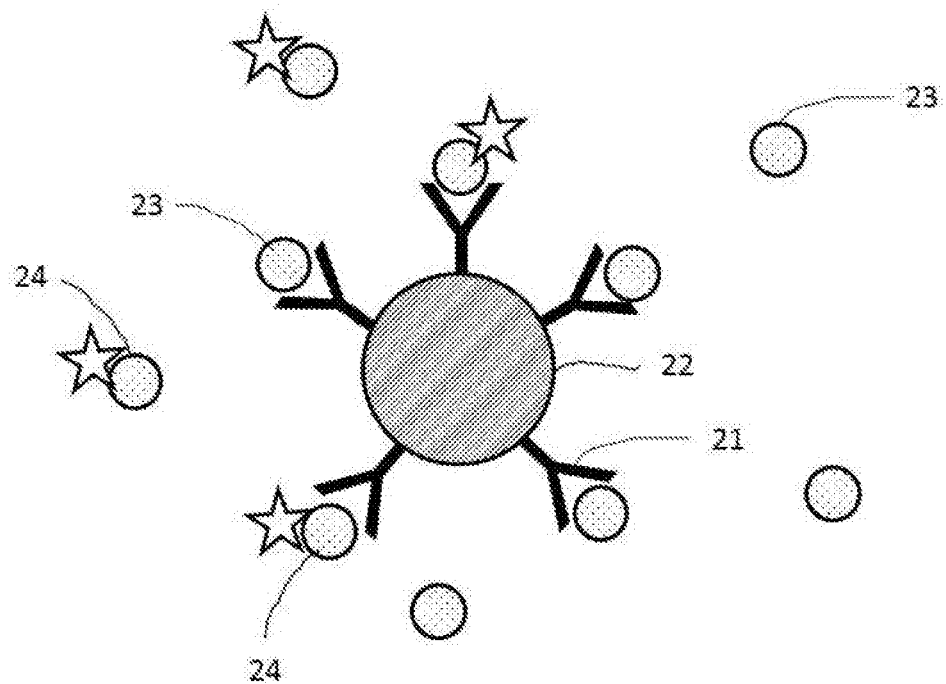
FIG. 2 shows a schematic diagram showing an antigen-antibody reaction system according to the second embodiment of the method according to the present invention.

The second embodiment is a one-step competition assay in which an anti-bicyclo PGE-MUM antibody-immobilized magnetic particles and a labeled bicyclo PGE-MUM antigen are used. The antigen-antibody reaction system according to the second embodiment is shown in FIG. 2. Magnetic particles 22 on which an anti-bicyclo PGE-MUM antibody 21 has been immobilized, a bicyclo PGE-MUM antigen 23 contained in a sample, and a labeled bicyclo PGE-MUM antigen 24 are allowed to coexist and react together and then are washed to detect the labeled antigen 24 bound to the magnetic particles 22 through the antibody 21. The higher the concentration of the antigen 23 in the sample, the smaller the amount of the labeled antigen 24 binding to the magnetic particles 22 through the antibody 21 and thus the lower the obtained signal.

The present embodiment has the same various conditions as those of the first embodiment, except that the antibody, instead of the antigen, is immobilized on the magnetic particles and the antigen, instead of the antibody, is labeled.

Third Embodiment

Figure 3:
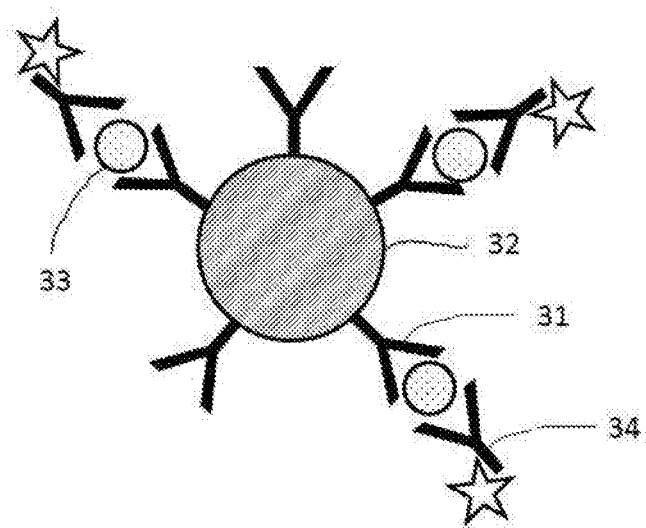
FIG. 3 shows a schematic diagram showing an antigen-antibody reaction system according to the third embodiment of the method according to the present invention.

The third embodiment is a two-step sandwich assay in which an anti-bicyclo PGE-MUM antibody-immobilized magnetic particles and a labeled anti-bicyclo PGE-MUM antibody are used. The antigen-antibody reaction system according to the third embodiment is shown in FIG. 3. Magnetic particles 32 on which an anti-bicyclo PGE-MUM antibody 31 has been immobilized and a bicyclo PGE-MUM antigen 33 contained in a sample react together, are washed, and then react with a labeled anti-bicyclo PGE-MUM antibody 34, and then are washed to detect the labeled antibody 34 bound to the magnetic particles 32 through the antibody 31 and the antigen 33. The higher the concentration of the antigen 33 in the sample, the larger the amount of the labeled antibody 34 bound to the magnetic particles 32 and thus the higher the obtained signal.

The present embodiment has the same various conditions as those of the first embodiment, except that the antibody, instead of the antigen, is immobilized on the magnetic particles and the magnetic particles are washed prior to the reaction with the labeled antibody.

Fourth Embodiment

Figure 4:
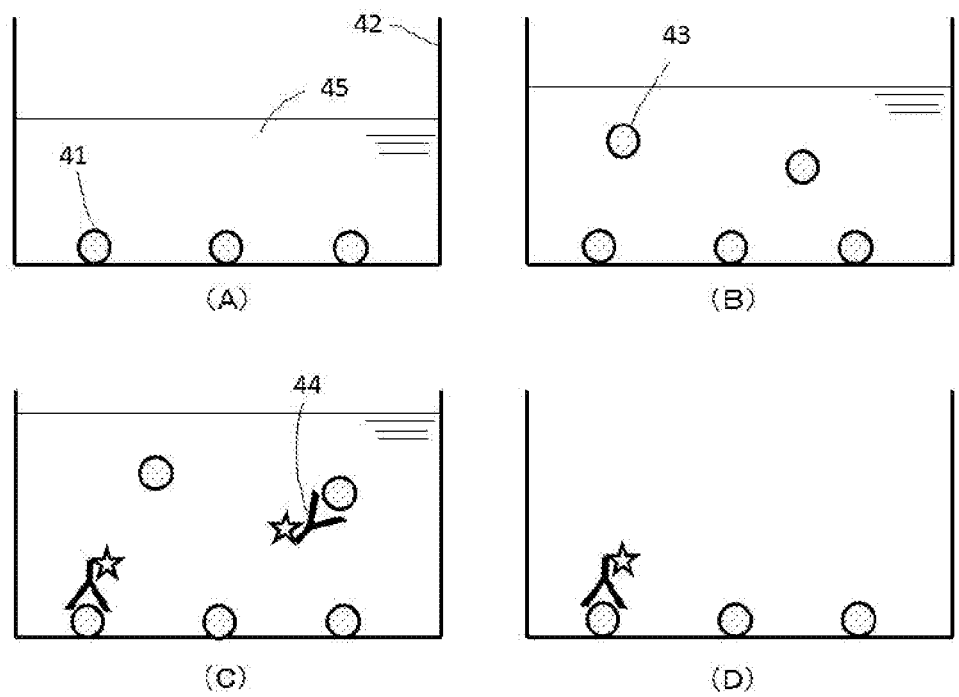
FIG. 4 shows a schematic diagram showing an antigen-antibody reaction system according to the fourth embodiment of the method according to the present invention.

The fourth embodiment is a one-step competitive ELISA in which a bicyclo PGE-MUM antigen-immobilized microwell plate and a labeled anti-bicyclo PGE-MUM antibody are used. The antigen-antibody reaction system according to the fourth embodiment is shown in FIG. 4. A microwell plate 42 on which a bicyclo PGE-MUM antigen 41 has been immobilized is filled with a sample treatment solution 45 containing a pH buffering agent and a cationic surfactant (FIG. 4A) and then a urinary mixture (sample) is added thereto (FIG. 4B). A labeling solution containing a labeled anti-bicyclo PGE-MUM antibody 44 is further added thereto (FIG. 4C). The labeled antibody 44 reacts with the immobilized antigen 41 and an antigen 43 contained in the sample, and the labeled antibody 44 bound to the immobilized antigen 41 is detected after washing the plate (FIG. 4D). The higher the concentration of the antigen 43 contained in the sample, the smaller the amount of the labeled antibody 44 bound to the immobilized antigen 41 and thus the lower the obtained signal.

The present embodiment has the same various conditions as those of the first embodiment, except that the antigen is immobilized not on magnetic particles but on a microwell plate and the sample treatment solution without any magnetic particles is used instead of a magnetic particle buffer.

With regard to the microwell plate used in the present embodiment, any known microwell plate commonly used in enzyme immunoassays (for example, ELISA) can be used regardless of its shape, material and dimensions.

Fifth Embodiment

Figure 5:
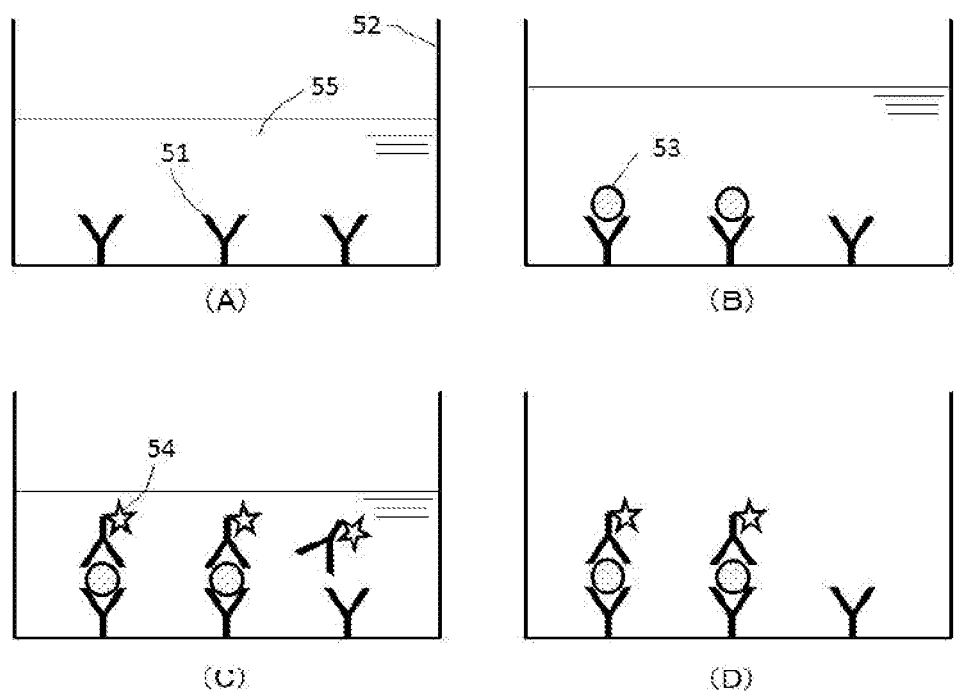
FIG. 5 shows a schematic diagram showing an antigen-antibody reaction system according to the fifth embodiment of the method according to the present invention.

The fifth embodiment is a two-step sandwich ELISA in which an anti-bicyclo PGE-MUM antibody-immobilized microwell plate and a labeled anti-bicyclo PGE-MUM antibody are used. The antigen-antibody reaction system according to the fifth embodiment is shown in FIG. 5. A microwell plate 52 on which an anti-bicyclo PGE-MUM antibody 51 has been immobilized is filled with a sample treatment solution 55 containing a pH buffering agent and a cationic surfactant (FIG. 5A) and then a urinary mixture (sample) is added thereto to react a bicyclo PGE antigen 53 in the sample with the antibody 51 (FIG. 5B). The microwell plate 52 is washed and then a labeling solution containing a labeled anti-bicyclo PGE-MUM antibody 54 is added thereto and allowed to react (FIG. 5C). The microwell plate is washed and the labeled antibody 54 bound to the antibody 51 through the antigen 53 is detected (FIG. 5D). The higher the concentration of the antigen 53 contained in the sample, the larger the amount of the labeled antibody 54 bound to the antibody 51 and thus the higher the obtained signal.

The present embodiment has the same various conditions as those of the fourth embodiment, except that the antibody, instead of the antigen, is immobilized on the microwell plate and a sandwich assay is applied instead of a competition assay.

Further Embodiments

The present invention is not limited to the first to fifth embodiments, but may be practiced with appropriately making changes in the material and shape of the solid phase to which an antigen or an antibody is bound, the combination of the immobilized antigen/antibody and the labeled antibody/antigen, and the conditions of the one-step/two-step competition/sandwich assay.

A cationic surfactant in a magnetic particle buffer (or a sample treatment solution) may cause reduction in stability of an antibody depending on the nature of the used antibody and, thus, a system in which an antigen, rather than an antibody, has been immobilized may be more preferable.

A Kit for the Measurement of the Prostaglandin E Main Urinary Metabolite (PGE-MUM)

The kit according to the present invention comprises a solid phase on which a bicyclo PGE-MUM or an anti-bicyclo PGE-MUM antibody is immobilized; a second pH buffering agent which exerts a buffering effect in the basic range in a weakly-acidic basal buffer solution which is different from the pH buffering agent contained in the basal buffer solution; and a cationic surfactant. In addition to these, a labeled antibody solution as described above, an alkaline aqueous solution for alkaline treatment, and a standard solution for standard curve preparation may be provided. Examples of the solid phase include particles, preferably magnetic particles, and the microplate, described above.

The standard solutions can be prepared by dissolving known amounts of bicyclo PGE-MUM in a known buffer solution, such as Tris or phosphate buffer. A set of standard solutions can be prepared to have 2 to 10 different concentrations in the range from 0 to 300 ng/mL but it is not limited to those conditions.

The present invention will be described specifically by way of examples. However, the present invention is not limited to the following examples.

Reference Example 1

Measurement by Conventional Method (Radioimmunoassay (RIA))

Measurement of PGE-MUM was performed on 8 urine samples from volunteers by a conventional method.

A 50-μL urine sample was mixed with 100 μL of 1 N NaOH and the resulting mixture was left to stand at room temperature for 30 minutes. The mixture was neutralized by adding 100 μL of 1 N hydrochloric acid thereto, and the mixture was further supplemented with and diluted with 1000 μL of an assay buffer (composition: 50 mM phosphate buffer (pH 7.2), 0.1% gelatin, and 0.1% sodium azide). A 100-μL aliquot was withdrawn from 1250 μL of the diluted mixture and mixed with 100 μL of a tracer solution (composition: $^{125}$I-labeled bicyclo PGE-MUM, and the assay buffer) containing a known concentration of a $^{125}$I-labeled bicyclo PGE-MUM. Furthermore, 100 μL of a rabbit anti-bicyclo PGE-MUM antiserum solution (composition: an antiserum, and the assay buffer) was added thereto and the resulting mixture was left to stand at room temperature for two hours. Then, a separation solution containing anti-rabbit IgG antibody-immobilized magnetic particles (composition: the antibody-immobilized magnetic particles at 0.02% (w/v), and the assay buffer) was added thereto and the resulting mixture was left to stand at room temperature for 15 minutes. The magnetic particles were collected and washed to remove components unbound to the magnetic particles, and the remaining $^{125}$I (bound to the magnetic particles) was counted. The PGE-MUM value in the urine sample was calculated based on a standard curve from the above count. Similarly to the sample, the radioactivity count was measured for standard solutions each containing an amount of bicyclo PGE-MUM corresponding to 0, 2.05, 6.25, 18.5, 55.5, 166.5, or 500 ng/mL in terms of the amounts before dilution, and a standard curve was prepared based on the obtained counts from the respective standard solutions.

Comparative Example 1 Measurement by Chemiluminescent Enzyme Immunoassay (CLEIA) with Neutralization and Dilution Steps (No Cationic Surfactant)

Measurement of PGE-MUM was performed on the same 8 urine samples from volunteers as in Reference Example 1 by the following method. A 50-μL urine sample was mixed with 100 μL of 1 N NaOH and the resulting mixture was left to stand at room temperature for 30 minutes. The mixture was neutralized by adding 100 μL of 1 N hydrochloric acid thereto and mixing the resulting mixture, and the mixture was further supplemented with and diluted with 1000 μL of a RIA assay buffer (composition: 9.5 mM sodium dihydrogen phosphate dihydrate, 40.5 mM disodium hydrogen phosphate dodecahydrate, and gelatin, pH 7.4). A 10-μL aliquot was withdrawn from 1250 μL of the diluted mixture and mixed with 50 μL of a labeled antibody solution (composition: an ALP-labeled antibody, 50 mM Tris, 1 mM magnesium chloride, 0.1 mM zinc chloride, sucrose, and gelatin, pH 7.4) containing an alkaline phosphatase (ALP)-labeled mouse anti-bicyclo PGE-MUM monoclonal antibody and the resulting mixture was allowed to react at 37° C. for 8 minutes. A 50-μL magnetic particle buffer containing bicyclo PGE-MUM antigen-immobilized magnetic particles (composition: the antigen-immobilized magnetic particles at 0.02% (w/v), 9.5 mM sodium dihydrogen phosphate dihydrate, 40.5 mM disodium hydrogen phosphate dodecahydrate, and gelatin, pH 7.4) was added thereto and the resulting mixture was allowed to react at 37° C. for 8 minutes. The magnetic particles were collected and washed to remove components unbound to the magnetic particles, and a substrate solution containing AMPPD (LUMIPULSE (registered trademark) substrate solution, Fujirebio Inc.) in a volume of 200 μL was added thereto. The intensity of luminescence generated by an enzymatic reaction was counted at a wavelength of 417 nm, and the PGE-MUM value in the urine sample was calculated based on a standard curve from the above count. Similarly to the sample, the luminescence intensity was measured for standard solutions each containing an amount of bicyclo PGE-MUM corresponding to 0, 3, 10, 50, or 200 ng of PGE-MUM per mL, and a standard curve was prepared based on the obtained amounts of luminescence from the respective standard solutions. The steps following the neutralization step in this Comparative Example were performed using the automated analyzer LUMIPULSE Presto 11 (registered trademark, Fujirebio Inc).

Comparative Example 2 Measurement by CLEIA with Omission of Neutralization and Dilution Steps (No Cationic Surfactant)

Measurement of PGE-MUM was performed on the same 8 urine samples from volunteers as in Reference Example 1 by the following method. A 10-µL urine sample was mixed with 30 µL of 0.3 N NaOH and the resulting mixture was allowed to react at 37° C. for 6.5 minutes. A 50-µL magnetic particle buffer containing bicyclo PGE-MUM-immobilized magnetic particles (composition: the antigen-immobilized magnetic particles at 0.02% (w/v), 219.25 mM sodium dihydrogen phosphate dihydrate, 30.75 mM disodium hydrogen phosphate dodecahydrate, 50 mM Tricine, 300 mM sodium chloride, and gelatin, pH 5.5) and, furthermore, a 50-µL labeled antibody solution (composition: an ALP-labeled antibody, 50 mM Tris, 1 mM magnesium chloride, 0.1 mM zinc chloride, sucrose, and gelatin, pH 7.4) containing an ALP-labeled mouse anti-bicyclo PGE-MUM monoclonal antibody were added thereto and the resulting mixture was allowed to react at 37° C. for 16 minutes. The magnetic particles were collected and washed to remove components unbound to the magnetic particles, and a substrate solution containing AMPPD (LUMIPULSE (registered trademark) substrate solution, Fujirebio Inc.) in a volume of 200 µL was added thereto. The intensity of luminescence generated by an enzymatic reaction was counted, and the PGE-MUM value in the urine sample was calculated based on a standard curve from the above count. Similarly to the sample, the luminescence intensity was measured for standard solutions each containing an amount of bicyclo PGE-MUM corresponding to 0, 3, 10, 50, or 200 ng of PGE-MUM per mL, and a standard curve was prepared based on the obtained amounts of luminescence from the respective standard solutions. All the steps following the alkaline treatment step in this Comparative Example were performed using the automated analyzer LUMIPULSE Presto II (registered trademark, Fujirebio Inc.).

Example 1

Measurement of PGE-MUM was performed on the same 8 urine samples from volunteers as used in Reference Example 1 by the following method. A 10-µL urine sample was mixed with 30 µL of 0.3 N NaOH and the resulting mixture was allowed to react at 37° C. for 6.5 minutes. A 50-µL magnetic particle buffer containing bicyclo PGE-MUM-immobilized magnetic particles (composition: the antigen-immobilized magnetic particles at 0.02% (w/v), 219.25 mM sodium dihydrogen phosphate dihydrate, 30.75 mM disodium hydrogen phosphate dodecahydrate, 50 mM Tricine, 300 mM sodium chloride, 5 mM $C_{16}$ alkyltrimethylammonium bromide (C16TAB), 2 mM CHAPS, and gelatin, pH 5.5) and, furthermore, a 50-µL labeled antibody solution (composition: an ALP-labeled antibody, 50 mM Tris, 1 mM magnesium chloride, 0.1 mM zinc chloride, sucrose, and gelatin, pH 7.4) containing an ALP-labeled mouse anti-bicyclo PGE-MUM monoclonal antibody were added thereto and the resulting mixture was allowed to react at 37° C. for 16 minutes. The magnetic particles were collected and washed to remove components unbound to the magnetic particles, and a substrate solution containing AMPPD (LUMIPULSE (registered trademark) substrate solution, Fujirebio Inc.) in a volume of 200 µL was added thereto. The intensity of luminescence generated by an enzymatic reaction was counted, and the PGE-MUM value in the urine sample was calculated based on a standard curve from the above count.

Figure 6:
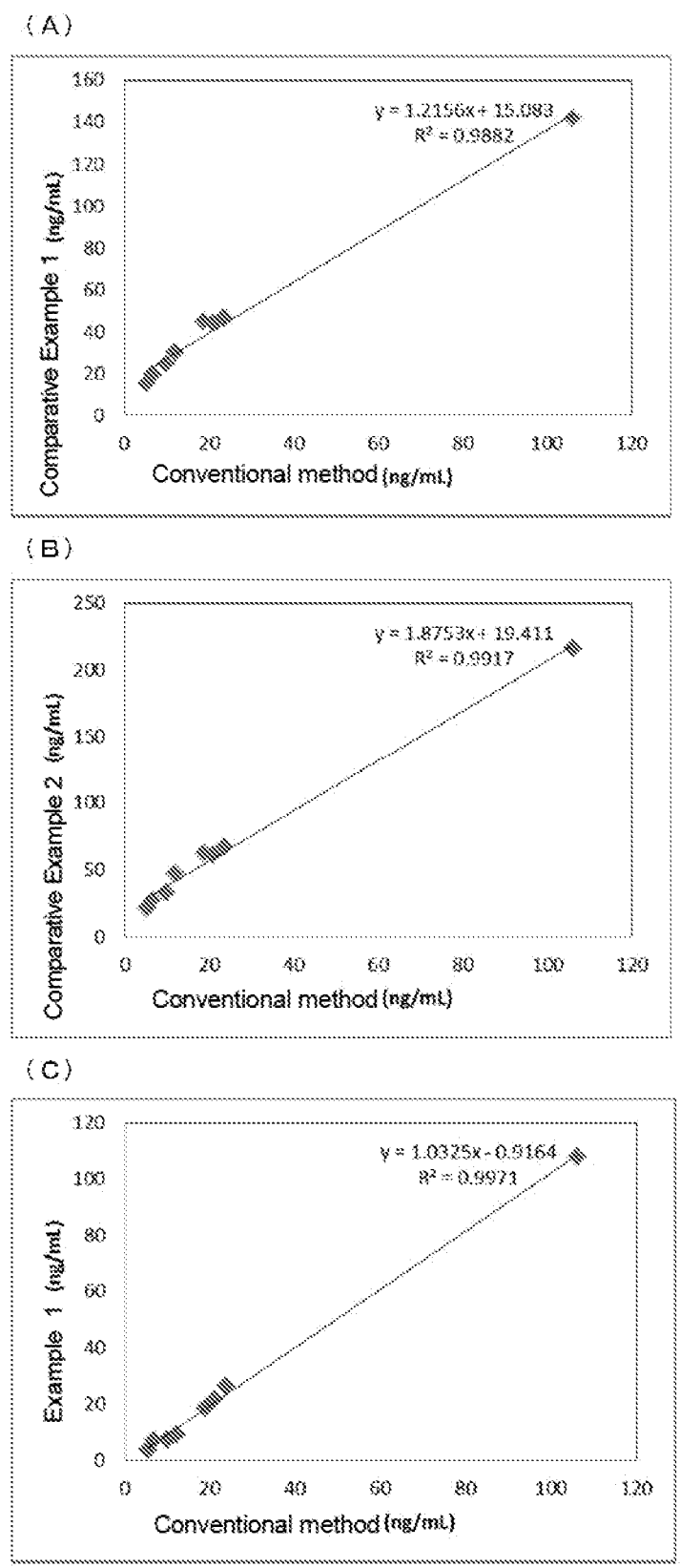
FIGS. 6A to 6C show the correlation between the measured PGE-MUM values obtained by a conventional method (RIA) and those obtained by each CLEIA method.

The measurement results from Reference Example 1, Comparative Example 1, Comparative Example 2 and Example 1 are shown in Table 1 and FIG. 6. FIG. 6A shows the correlation between the measurement result of Reference Example 1 and that of Comparative Example 1, and FIG. 6B shows the correlation between the measurement result of Reference Example 1 and that of Comparative Example 2, and FIG. 6C shows the correlation between the measurement result of Reference Example 1 and that of Example 1.

TABLE 1

| | | Comparative Example 1 | | Comparative Example 2 | | Example 1 | |
| --- | --- | --- | --- | --- | --- | --- | --- |
| Sample No. | Reference Example 1 (conventional method) Measured value (ng/mL) | Measured value (ng/mL) | Percentage relative to value measured by conventional method (%) | Measured value (ng/mL) | Percentage relative to value measured by conventional method (%) | Measured value (ng/mL) | Percentage relative to value measured by conventional method (%) |
| 1 | 6.88 | 19.7 | 286 | 27.8 | 404 | 7.60 | 110 |
| 2 | 9.95 | 24.6 | 247 | 33.2 | 334 | 7.30 | 73.4 |
| 3 | 106 | 142 | 134 | 216 | 204 | 108 | 102 |
| 4 | 18.8 | 45.1 | 240 | 62.9 | 335 | 18.9 | 101 |
| 5 | 20.9 | 44.2 | 211 | 61.3 | 293 | 21.7 | 104 |
| 6 | 5.28 | 15.4 | 292 | 21.3 | 403 | 3.70 | 70.1 |
| 7 | 23.7 | 46.9 | 198 | 67.1 | 283 | 26.6 | 112 |
| 8 | 12.2 | 30.4 | 249 | 47.7 | 391 | 9.20 | 75.4 |

In the cases where the CLEIA assays were used, a result relatively close to that from the conventional method (Reference Example 1) is obtained by performing the neutralization and dilution steps (Comparative Example 1). On the other hand, when the neutralization and dilution steps were omitted (Comparative Example 2), reduction or inhibition of immune reaction by the strong alkali was not observed because of the effects of the buffering agents but rather, a tendency to provide a significantly higher measurement value than that obtained by the conventional method was observed. It was inferred that this result was caused by an increased influence of contaminants in urine due to the omission of the dilution step. When $C_{7-16}$ surfactants each containing an anionic group were added to artificial urine and then the measurement was performed on those resulting mixtures, high measurement values similar to the above value were obtained (data not shown). Therefore, it was inferred that urinary contaminants having physical properties close to those of the above surfactants affected the measurement values. On the other hand, it was confirmed that use of the method of Example 1 gave a result almost equal to that from the conventional method, with regard to the measured PGE-MUM values. It is understood that this result was caused by a reduced influence of urinary contaminants (which are speculated to have an anionic group) due to the addition of the cationic surfactant. Accordingly, addition of a cationic surfactant enabled measurement of PGE-MUM without an influence of urinary contaminants in alkaline treated samples, with omission of neutralization and dilution steps.

Example 2 Test for the Effects of Various Cationic Substances

Measurement of PGE-MUM was performed on 4 urine samples under the same conditions as in Comparative Example 2, except that an alkyltrimethylammonium bromide (C12TAB, C14TAB, or C16TAB), or an alkyltrimethylammonium chloride (C14TAC, C16TAC, or C18TAC) was added to a concentration of 1 mM in a magnetic particle buffer. The results of the PGE-MUM measurement using the magnetic particle buffers each supplemented with a different cationic substance are shown in Table 2. In any of the measurements, a tendency to provide a lower measurement value compared to the measurement value of Comparative Example 2 in which no cationic substance was added was observed, while a tendency to provide a measurement value close to that obtained by the conventional method was observed particularly in the cases of using C16TAB, C14TAB, and C18TAC, respectively.

Additionally, besides the above-described cationic substances, inorganic cationic substances such as metal ions and low-molecular-weight cationic substances were added at a similar concentration to examine their effects but none of the cationic substances showed the effect to reduce the measurement value of PGE-MUM as seen in C16TAB (data not shown).

Accordingly, it was suggested that addition of an organic cationic substance, particularly a cationic surfactant whose number of carbon atoms is equal to or above a certain number, was effective to avoid the influence of urinary contaminants.

TABLE 2

| Sample No. | Conventional method Measured value (ng/mL) | C12TAB Measured value (ng/mL) | C12TAB Percentage relative to value measured by conventional method (%) | C14TAB Measured value (ng/mL) | C14TAB Percentage relative to value measured by conventional method (%) | C16TAB Measured value (ng/mL) | C16TAB Percentage relative to value measured by conventional method (%) |
| --- | --- | --- | --- | --- | --- | --- | --- |
| 1 | 6.88 | 24.7 | 359 | 14.8 | 215 | 11.2 | 163 |
| 2 | 9.95 | 30.2 | 304 | 16.3 | 164 | 12.4 | 125 |
| 3 | 106 | High | — | 169 | 159 | 134 | 126 |
| 4 | 18.8 | 62.7 | 334 | 40.3 | 214 | 27.8 | 148 |

| Sample No. | Conventional method Measured value (ng/mL) | C14TAC Measured value (ng/mL) | C14TAC Percentage relative to value measured by conventional method (%) | C16TAC Measured value (ng/mL) | C16TAC Percentage relative to value measured by conventional method (%) | C18TAC Measured value (ng/mL) | C18TAC Percentage relative to value measured by conventional method (%) |
| --- | --- | --- | --- | --- | --- | --- | --- |
| 1 | 6.88 | 14.9 | 217 | 18.1 | 263 | 11.3 | 164 |
| 2 | 9.95 | 17.1 | 172 | 19.9 | 200 | 12.1 | 122 |
| 3 | 106 | 180 | 170 | 189 | 178 | 159 | 150 |
| 4 | 18.8 | 36.8 | 196 | 43.7 | 232 | 29.2 | 155 |

Example 3 Study on Cationic Surfactant Concentration

The surfactant which was most effective in avoiding the influence of urinary contaminants as seen in Table 2, C16TAB, was used to study the optimal concentration.

Measurement of PGE-MUM was performed similarly to Comparative Example 2 on the 8 urine samples shown in Table 1, except that C16TAB was added to a concentration of 1.0, 2.0, or 3.0 mM in the magnetic particle buffer. The respective measured values are shown in Table 3. It was found that a higher concentration of C16TAB added to the magnetic particle buffer tended to produce a smaller measurement value, which is a measurement value close to that obtained by the conventional method. On the other hand, when the concentration of C16TAB was more than 3.0 mM, C16TAB was hardly dissolved and also showed a tendency to precipitate over time after preparation of the magnetic particle buffer and thus to easily cause reduction of the luminescence intensity in the measurement system (data not shown).

TABLE 3

| | Conventional method | C16TAB concentration | | | | | | |
|---|---|---|---|---|---|---|---|---|
| | | 1.0 mM | | | 2.0 mM | | 3.0 mM | |
| Sample No. | Measured value (ng/mL) | Measured value (ng/mL) | Percentage relative to value measured by conventional method (%) | Measured value (ng/mL) | Percentage relative to value measured by conventional method (%) | Measured value (ng/mL) | Percentage relative to value measured by conventional method (%) | |
| 1 | 6.88 | 13.4 | 195 | 10.9 | 158 | 8.70 | 127 | |
| 2 | 9.95 | 14.7 | 148 | 12.2 | 123 | 9.10 | 91.5 | |
| 3 | 106 | 130 | 123 | 115 | 109 | 94.0 | 88.7 | |
| 4 | 18.8 | 31.5 | 168 | 26.2 | 139 | 22.4 | 119 | |
| 5 | 20.9 | 34.7 | 166 | 29.3 | 140 | 24.4 | 117 | |
| 6 | 5.28 | 7.00 | 133 | 5.60 | 106 | 4.40 | 83.3 | |
| 7 | 23.7 | 39.7 | 168 | 33.3 | 141 | 28.6 | 121 | |
| 8 | 12.2 | 19.6 | 161 | 14.8 | 121 | 10.6 | 86.9 | |
| Average | — | — | 158 | — | 130 | — | 104 | |

Example 4 Addition of a Zwitterionic Surfactant to a Magnetic Particle Buffer

Further addition of another surfactant to the magnetic particle buffer was studied in order to suppress the precipitation of a cationic surfactant (C16TAB) in the magnetic particle buffer and to stably provide a suppressive effect on increase in measurement values.

The magnetic particle buffer of Comparative Example 2 was supplemented with C16TAB at 2 mM and a zwitterionic surfactant (CHAPS) at 0.1 mM or 1.0 mM or a nonionic surfactant (Brij 35) at 0.1 mM or 1.0 mM to prepare mixtures. For 4 days, a portion of each mixture was left to stand at 4° C. and another portion of each mixture was left to stand at 37° C. Besides, a magnetic particle buffer containing neither zwitterionic surfactant nor nonionic surfactant was also prepared as a blank. Measurement was performed on 4 urine samples under the same conditions as in Comparative Example 2, except that these magnetic particle buffers were used.

The measurement results are shown in Table 4-1 to Table 4-3. In the magnetic particle buffers to which the nonionic surfactant Brij 35 was added, the addition of the surfactant at 1.0 mM prevented the precipitation of C16TAB and resulted in showing an improved stability, but the effect of C16TAB to suppress an increase in background level was reduced. On the other hand, in the magnetic particle buffers to which the zwitterionic surfactant CHAPS was added, the addition of the surfactant at 1.0 mM prevented the precipitation of C16TAB and resulted in showing an improved stability, and the effect of C16TAB to suppress an increase in background level was maintained.

TABLE 4-1

| | Conventional method | Blank | | | | |
|---|---|---|---|---|---|---|
| | | Luminescence count | | | Measured value (ng/mL) | |
| Sample No. | Measured value (ng/mL) | Mixture stored at 4° C. | Mixture stored at 37° C. | Ratio between mixtures stored at 37° C. and at 4° C. (%) | Mixture stored at 4° C. | Percentage relative to value measured by Conventional method (%) |
| 1 | 6.88 | 546028 | 377058 | 69.1 | 9.10 | 132 |
| 2 | 9.95 | 539574.0 | 353145 | 65.4 | 9.20 | 92.5 |
| 3 | 106 | 68161 | 45328 | 66.5 | 119 | 112 |
| 4 | 18.8 | 273259 | 177941 | 65.1 | 23.2 | 123 |

TABLE 4-2

| | Conventional method Measured value (ng/mL) | Brij 35 concentration | | | | | | | | | |
|---|---|---|---|---|---|---|---|---|---|---|---|
| | | 0.1 mM | | | | | 1.0 mM | | | | |
| | | Luminescence count | | | Measured value (ng/mL) | | Luminescence count | | | Measured value (ng/mL) | |
| Sample No. | | Mixture stored at 4° C. | Mixture stored at 37° C. | Ratio between mixtures stored at 37° C. and at 4° C. (%) | Mixture stored at 4° C. | Percentage relative to value measured by Conventional method (%) | Mixture stored at 4° C. | Mixture stored at 37° C. | Ratio between mixtures stored at 37° C. and at 4° C. (%) | Mixture stored at 4° C. | Percentage relative to value measured by Conventional method (%) |
| 1 | 6.88 | 575315 | 409654 | 71.2 | 11.3 | 164 | 604096 | 551348 | 91.3 | 11.1 | 161 |
| 2 | 9.95 | 574768 | 406428 | 70.7 | 11.3 | 114 | 609212 | 551544 | 90.5 | 11.0 | 111 |

TABLE 4-2-continued

| | | Brij 35 concentration | | | | | | | | | |
|---|---|---|---|---|---|---|---|---|---|---|---|
| | | 0.1 mM | | | | | | 1.0 mM | | | |
| | | Measured value (ng/mL) | | | | | | | | | Measured value (ng/mL) |
| | | | | | | Percentage | | | | | |
| | Conventional | Luminescence count | | | | relative | Luminescence count | | | | Percentage |
| Sample No. | method Measured value (ng/mL) | Mixture stored at 4° C. | Mixture stored at 37° C. | Ratio between mixtures stored at 37° C. and at 4° C. (%) | Mixture stored at 4° C. | to value measured by Conventional method (%) | Mixture stored at 4° C. | Mixture stored at 37° C. | Ratio between mixtures stored at 37° C. and at 4° C. (%) | Mixture stored at 4° C. | relative to value measured by Conventional method (%) |
| 3 | 106 | 72762 | 54617 | 75.1 | 177.2 | 167 | 72521 | 71143 | 98.1 | 167 | 158 |
| 4 | 18.8 | 287557 | 204464 | 71.1 | 31.2 | 166 | 293577 | 268067 | 91.3 | 29.6 | 157 |

TABLE 4-3

| | | CHAPS concentration | | | | | | | | | |
|---|---|---|---|---|---|---|---|---|---|---|---|
| | | 0.1 mM | | | | | | 1.0 mM | | | |
| | | Measured value (ng/mL) | | | | | | | | | Measured value (ng/mL) |
| | | | | | | Percentage | | | | | |
| | Conventional | Luminescence count | | | | relative | Luminescence count | | | | Percentage |
| Sample No. | method Measured value (ng/mL) | Mixture stored at 4° C. | Mixture stored at 37° C. | Ratio between mixtures stored at 37° C. and at 4° C. (%) | Mixture stored at 4° C. | to value measured by Conventional method (%) | Mixture stored at 4° C. | Mixture stored at 37° C. | Ratio between mixtures stored at 37° C. and at 4° C. (%) | Mixture stored at 4° C. | relative to value measured by Conventional method (%) |
| 1 | 6.88 | 556088 | 394035 | 70.9 | 10.3 | 150 | 533963 | 492599 | 92.3 | 10.2 | 148 |
| 2 | 9.95 | 556763 | 411981 | 74.0 | 9.60 | 96 | 545749 | 480073 | 88.0 | 9.80 | 98.5 |
| 3 | 106 | 67245 | 44907 | 66.8 | 175 | 165 | 69925 | 56076 | 80.2 | 146 | 137 |
| 4 | 18.8 | 282573 | 203785 | 72.1 | 26.0 | 138 | 278466 | 232195 | 83.4 | 26.4 | 140 |

INDUSTRIAL APPLICABILITY

The method and kit according to the present invention are used to measure the main metabolite of human prostaglandin E in urine and are useful for determining, for example, the stage of ulcerative colitis, whether remission phase or not, and the stage of interstitial pneumonia, and thus can be widely used in medical field.

The invention claimed is:

1. A method of measuring prostaglandin E main urinary metabolite (PGE-MUM), said method comprising the steps of:
  a) mixing a urine sample with an alkaline aqueous solution to form a mixture solution, and
  b) subjecting the mixture solution resulting from a) to an immunoassay in order to measure PGE-MUM in the urine sample,
  wherein said immunoassay is performed in a basal buffer solution comprising a first pH buffering agent, a second pH buffering agent having a pKa of from 7.0 to 10.0, and a cationic surfactant; wherein the second pH buffering agent is different from the first pH buffering agent, and wherein the pH of the basal buffer solution is from 5.0 to 6.0; and
  wherein said immunoassay comprises using a labeled anti-bicyclo PGE-MUM antibody and particles on which either bicyclo PGE-MUM or an anti-bicyclo PGE-MUM antibody is immobilized, wherein said particles are suspended in said basal buffer solution.

2. The method of claim 1, wherein said cationic surfactant is an alkyltrimethylammonium halide.

3. The method of claim 2, wherein the alkyl group in said alkyltrimethylammonium halide has 12 to 20 carbon atoms.

4. The method of claim 1, wherein said particles suspended in said basal buffer solution are mixed with the mixture solution resulting from a).

5. The method of claim 4, wherein said particles are magnetic particles.

6. The method of claim 4, wherein said basal buffer solution further comprises a zwitterionic surfactant.

7. The method of claim 6, wherein the molar concentration of the zwitterionic surfactant is 10 to 90% of the molar concentration of the cationic surfactant.

8. The method of claim 1, wherein said bicyclo PGE-MUM is immobilized on said particles, and said step b) comprises reacting the mixture solution resulting from a) with said particles suspended in said basal buffer solution to form a reaction solution, and then reacting the resulting reaction solution with a labeling solution containing the labeled anti-bicyclo PGE-MUM antibody, washing said particles, and then quantifying labeled anti-bicyclo PGE-MUM antibody immobilized on said particles.

9. The method of claim 1, wherein the method does not comprise an additional step of neutralizing or diluting the mixture solution resulting from a).

10. A kit for the measurement of urinary PGE-MUM, comprising:
- a basal buffer solution comprising a first pH buffering agent, a second pH buffering agent having a pKa of from 7.0 to 10.0, and a cationic surfactant; wherein the second pH buffering agent is different from the first pH buffering agent, and wherein the pH of the basal buffer solution is from 5.0 to 6.0;
- particles on which bicyclo PGE-MUM or an anti-bicyclo PGE-MUM antibody is immobilized, wherein said particles are suspended in said basal buffer solution; and
- a labeled anti-bicyclo PGE-MUM antibody.

11. The kit of claim 10, wherein said particles are magnetic particles.

12. The kit of claim 10, wherein said basal buffer solution further comprises a zwitterionic surfactant.

13. The kit of claim 10, wherein said cationic surfactant is an alkyltrimethylammonium halide.

14. The kit of claim 13, wherein the alkyl group in said alkyltrimethylammonium halide has 12 to 20 carbon atoms.

15. The kit of claim 12, wherein the molar concentration of the zwitterionic surfactant is 10 to 90% of the molar concentration of the cationic surfactant.

* * * * *